United States Patent [19]

Mochida

[11] Patent Number: 4,960,566
[45] Date of Patent: Oct. 2, 1990

[54] CHEMICAL REACTION APPARATUS
[75] Inventor: Ei Mochida, Tokyo, Japan
[73] Assignee: Mochida Pharmaceutical Co., Ltd., Tokyo, Japan
[21] Appl. No.: 87,646
[22] Filed: Aug. 19, 1987
[30] Foreign Application Priority Data
  Sep. 11, 1986 [JP] Japan .................................. 61-214521
  Mar. 16, 1987 [JP] Japan ............................... 62-39030[U]
[51] Int. Cl.⁵ .............................................. G01N 35/04
[52] U.S. Cl. ........................................ 422/65; 422/73; 422/100; 435/289; 73/864.72
[58] Field of Search ..................... 422/65, 66, 67, 100, 422/73; 436/44; 435/289

[56] References Cited

U.S. PATENT DOCUMENTS

| | | | |
|---|---|---|---|
| 3,490,876 | 1/1970 | Auphan et al. | 422/66 |
| 3,607,097 | 9/1971 | Auphan et al. | 422/65 |
| 3,859,051 | 1/1975 | Natelson | 422/65 |
| 3,918,908 | 11/1975 | Moyer et al. | 422/73 |
| 4,040,533 | 8/1977 | De Boer et al. | |
| 4,052,161 | 10/1977 | Atwood et al. | 422/64 |
| 4,058,367 | 11/1977 | Gilford | 422/67 |
| 4,113,436 | 9/1978 | Werder | 422/67 |
| 4,349,510 | 9/1982 | Kolehmainen | 422/66 |

FOREIGN PATENT DOCUMENTS 0182221 5/1986 European Pat. Off.
  WO83/1119 3/1983 PCT Int'l Appl.

Primary Examiner—Michael S. Marcus
Attorney, Agent, or Firm—Cushman, Darby & Cushman

[57] ABSTRACT

A chemical reaction apparatus having a plurality of capillary tubes and a conveying device for holding the tubes substantially horizontal such as to convey the tubes. A feeding device for reagent and the like is mounted on the conveying device and feeds a reagent and the like for use in a chemical reaction to the interior of the capillary tubes. Thereafter the reagent and the like remains in a stable condition with these discharged into the entire length of each of the tubes.

25 Claims, 6 Drawing Sheets

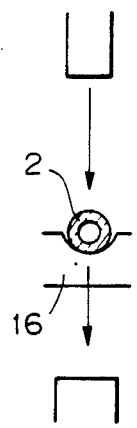
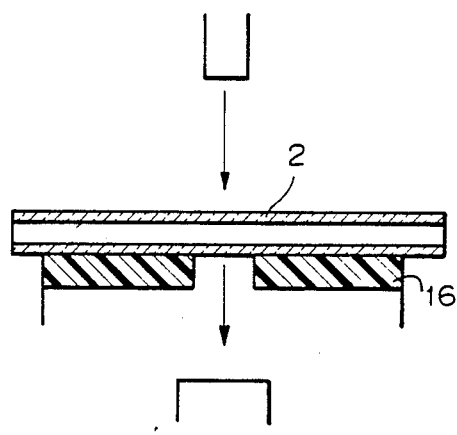
Fig. 11a  Fig. 11b
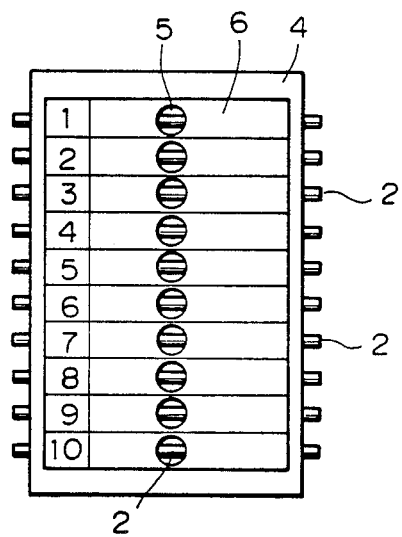
Fig. 12

CHEMICAL REACTION APPARATUS

BACKGROUND OF THE INVENTION

1. Field of the Invention

This invention relates to a chemical reaction apparatus which is not only applicable to certain fields within the chemical industry such as biotechnology, biochemistry and the like, but is also suitable for carrying out research in biological chemistry, inclusive of microbiology, or various kinds of chemical reaction tests such as a clinical diagnosis. The invention relates more particularly to a chemical reaction apparatus which is adapted to allow chemical reaction in a capillary tube so that a reaction test may be made in a simple and efficient manner.

2. Description of the Related Art

In general, methods and apparatus for performing a chemical reaction by the use of many samples each in a small quantity have recently shown rapid progress in the development of techniques in the domain of clinical diagnosis for use with immunochemical reactions. One of these methods has proposed the fixing of an immunoreactive substance on a tiny bead of plastic.

Other methods have been disclosed in such printed publications as European Patent Publication No. 0182221-A2, the inventor of which is also that of the instant application. A reaction container for use with the apparatus in which the aforementioned method is carried out employs test tubes which are tilted and rotated such as to significantly reduce the reaction time. This will fulfil the object of automatically treating many objects to be tested at a higher speed.

Arts and apparatus using capillary tubes have been suggested for performing an immunoreaction, one of which is disclosed in, for example, International Publication (PCT) No. W083/01119. The apparatus according to this PCT invention is fabricated in such a manner that a plurality of capillary tubes are vertically mounted on the periphery of a rotary bed to allow, an immunoreaction to be performed in the capillary tubes. The advantages derived from this apparatus lie in the fact that it is simple and compact since a rapid reaction in the capillary tubes eliminates the need for a stirring means.

When the blood of a patient is used as a sample as in an immunoreaction, tests on a given volume of blood have to be made for many items so that the volume of blood to be used for one item is gradually reduced. However, the aforementioned apparatus for performing a reaction in capillary tubes has an advantage in that a small volume sample is adequate to be useful as compared with the conventional apparatus.

The method for use with a tiny plastic bead is suitable for mass production wherein immunoreactive substances are themselves coated to be the surface thereof. The use of a bead for performing many immunoreactions requires a complicated series of operations such as casting the bead in the test tube, taking out the bead to wash from the test tube, recasting the bead and adding a reagent thereto and so on. For accommodating this, various approaches have heretofore been made. For instance, various automatic mechanisms have been proposed but they have required a complicated mechanism and much time for the reaction. They are not suitable for treatment of many specimens at a high rate.

The European Patent Publication No. 0182221-A2 discloses an apparatus which employs instead of the bead mentioned above a test tube on the inner surface of which the immunoreactive substance is coated, the test tube being tilted and rotated to significantly reduce the reaction time required. An apparatus of this class is most suitable for the purpose of automatically treating many specimens at a high rate as compared with the method for use with a bead.

However, this will render the operation of fixing the immunoreactive substance on the inside of the test tube very complicated and production costs will become high as compared with use of the surface of the bead. More specifically, this operation requires injection of a solution of the immunoreactive substance in a given quantity into the test tube such as to leave it as it is for a given time, and then removal of the solution from the inside, washing and drying the test tube, and so on. In contrast, according to the bead method, the object is effectively attained by casting many beads in the solution of the immunoreactive substance, and the subsequent washing and drying are readily facilitated to be made this method suitable for mass production For clinical examination, however the bead method is inconvenient to the user but ready for production whereas the tube method is convenient to the user but complicated in manufacture.

An operation for coating the immunoreactive substance on the inner surface of a capillary tube is very simple and easy as compared with the test tube operation. More specifically, it is similar in manner to the bead method in that a bundle of capillary tubes is vertically immersed in a solution of the immunoreactive substance so that the capillary tubes are readily filled with the solution from their lower ends to the center thereof. The capillary tubes are left as they are for a given time and at a certain temperature, and are then taken out for the washing and drying steps. Although the immunoreactive substance is coated to the exterior of the capillary tubes, the reaction may be performed without any difficulty when they are used with only the insides thereof involved in the reaction. And the capillary tube has a smaller diameter than that of the test tube so that the volume ratio of the coated immunoreactive substance to a liquid specimen is increased, resulting in a very quick reaction, and thereby eliminating the need for rotation of the test tube in order to facilitate the reaction as is necessary in the test tube method. For this reason, if an apparatus is devised which uses the capillary tubes such as to positively and simply handle a many specimens in an automatic manner, the capillary tube itself is tiny and the machine can thus be made compact so that quick mass treatment may be accomplished at a high treatment rate.

International Publication (PCT) No. W083/0119 discloses an apparatus for use with capillary tubes which employs a combination of coating the immunoreactive substance on the inner surface of the capillary tube and an automatic machine for successively performing the immunoreaction such as to improve on the well known method for coating various chemical substances to the inner surface of the capillary tube.

The apparatus disclosed in the aforementioned publication is constructed such that each of the capillary tubes is always held vertically for various operations. With this arrangement, when the reagent liquid to be charged in the capillary tube is increased the surface tension in the capillary tube cannot sustain the weight of the liquid even if the amount of the liquid is very small. Consequently a portion of the liquid flows out of the tube, thus preventing the apparatus from the performing an accurate chemical reaction.

When each of the capillary tubes is made of hydrophilic material such as glass and the lower end of each of the tubes is in contact with the surface of water, water is sucked into the tube by a capillary phenomenon and rises therein. The water rises to a level inversely proportional to the inner diameter of the tube. This will be shown in the following table prepared by the inventors of the subject application on the basis of their experiments.

TABLE

| inner diameter (mm) of glass capillary tube | raised level (mm) of water |
| --- | --- |
| 1.7 | 9.5 |
| 1.3 | 10.5 |
| 0.95 | 18.0 |

The length of the vertically held capillary tube which is capable of sustaining liquid with which it is completely filled is limited to what is shown in the table. The capillary tube to be used in the apparatus disclosed in the aforementioned publication thus must be quite short.

Sample and reagent liquids may be injected into each of the capillary tubes vertically held in this apparatus in such a manner that the liquid contained in a cup mounted on the top of the tube contacts the tube through perforation formed in the bottom of the cup.

In this connection, a longer capillary tube holds the liquid only in the lower portion thereof. Even if the capillary tube is short, the liquid drops fall from the lower end of the tube or are suspended therefrom when the volume of the liquid contained in the cap is more than the capacity of the tube. Thus, the volume of liquid which drains into a measuring system is inaccurate in quantity. In order to attain accuracy, an accurate micropump needs to be provided. It is, therefore, difficult to secure simplicity of structure with use of a capillary tube instead of a micropump as proposed in the aforementioned publication. Since an extremely short capillary tube has to be used, the mechanism for handling such capillary tube is necessarily complicated. Further, in the aforementioned apparatus, the capillary tube is held vertically and mounted on the periphery of the rotary base as a conveyor device. A specific device is required for mounting the tube and troubles are then involved in mounting and demounting the tube.

SUMMARY OF THE INVENTION

It is an object of the invention to provide a chemical reaction apparatus which is simple in structure and capable of allowing a chemical reaction with a reagent and the like to take place in such a manner that an accurate chemical reaction is performed, the structure being such that it is easy to mount and demount the capillary tube without requiring any stirring device and metering device for a reagent.

According to the present invention, there is provided a chemical reaction apparatus comprising: a plurality of capillary tubes, a conveying device for holding the capillary tubes substantially horizontal such as to convey said tubes, and a feeding device for reagent and the like mounted along said conveying device adapted to feed a reagent and the like for use in a chemical reaction to the interior of said capillary tubes.

In accordance with the chemical reaction apparatus of the present invention, the capillary tubes are always conveyed while being held in a horizontal position by the conveying device whereas the reagent and the like are fed to the interior of the tubes from the feeding device. If the reagent and the like contacts the ends of the capillary tubes, it is instantaneously charged into the tubes. At this moment, the capillary tubes are held substantially horizontal so that the force of gravity which tends to cause the liquid in the tube to drop from the tubes is smaller than the force of the surface tension by virtue of which the liquid is retained in the tubes. As a result, the reagent and the like remains in a stable condition while these discharged into the entire length of each of the tubes. The capillary tubes are each time supplied with a constant volume (equal to the internal volume of the tube) of the reagent and the like.

For this reason, the reagent and the like used in the chemical reaction are always maintained at a constant volume, thereby allowing accurate chemical reactions to be performed.

Further, since the capillary tubes are held and conveyed by the conveying device while in a horizontal position, the conveying procedure may be accomplished simply by laying the tubes on the conveying device. The device used for holding the tubes on the conveying device or demounting the tubes may thus be very simple.

BRIEF DESCRIPTION OF THE DRAWINGS

FIGS. 11a and 11b are schematic front and side views of another form of the light emission state in section as used in a measuring device, FIG. 12 is a back plan view of the sheet with the capillary tubes shown in FIG. 7.

DESCRIPTION OF THE PREFERRED EMBODIMENT

An embodiment in which the invention is applied to an immunoreactive apparatus will first be explained with reference to FIGS. 1, 2 and 3.

Figure 1:
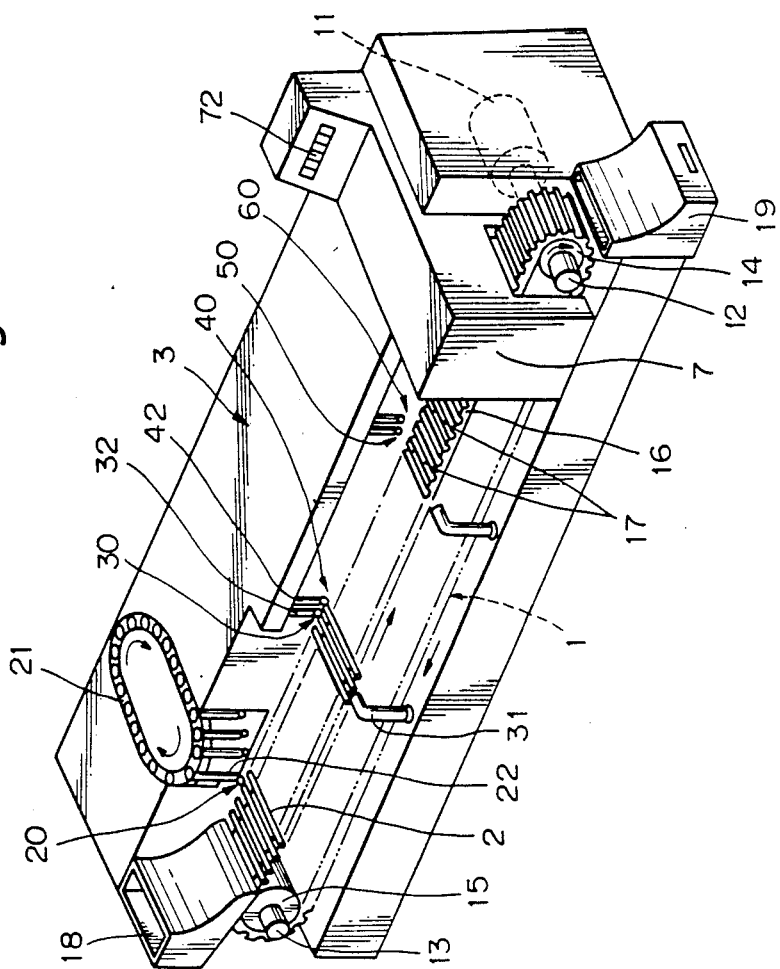
FIG. 1 is a perspective view of an apparatus embodying the present invention.
Figure 2:
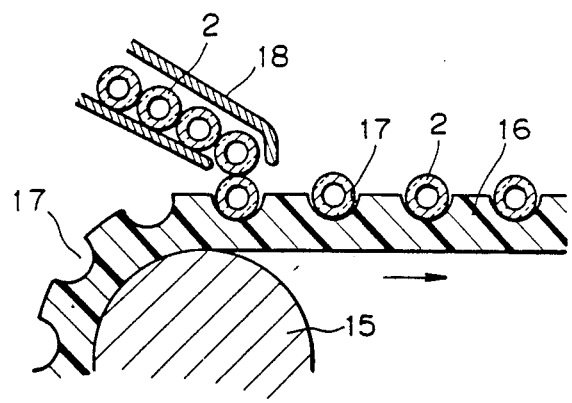
FIG. 2 is a fragmentary sectional view of the neighborhood of a hopper of the apparatus.

FIG. 1 is a perspective view of an apparatus according to an embodiment of the invention, wherein numeral 1 is a belt conveyor adapted for use as a device for conveying a plurality of capillary tubes 2 and comprises a drive shaft 12 driven by a motor 11 with a reduction gear, a driven shaft 13 rotatably supported on a body of the apparatus, the two shafts 12, 13 being mounted on the apparatus at opposite ends thereof, and an endless conveyor belt 16 of material such as polyurethane resin trained in parallel fashion over pulleys 14 and 15 mounted on the respective shafts 12, 13.

The motor 11 with the reduction gear is adapted to rotate the drive shaft 12 such as to put the upper run of the conveyor belt 16 in a stretched state. In FIG. 1, the drive shaft 12 is rotated in the clockwise direction. The motor 11 with the reduction gear may be rotated at a constant speed or intermittently rotated by means of microprocessor control. A detector device such as an optical sensor may be provided for detecting the position of the conveyor belt 16 such as to control rotation of the motor.

The conveyor belt 16 is mounted such as that its upper run is substantially horizontal. Grooves 17 are formed at a constant distance and perpendicular to the direction of the belt running on the periphery of the conveyor belt 16 whereby the capillary tubes 2 may be held in the grooves. Although the number of grooves 17 may be selected depending upon the object of a particular application, 30–200 may be regarded as preferable. In this connection, it is noted that a timing belt with corrugations formed on the inside thereof is used as the conveyor belt 16 such as to mesh with pulleys which are also corrugated. This will avoid slippage between the belt and the pulleys. The grooves 17 may take any configuration so long as the capillary tubes 2 may be stably held therein. For instance, a plurality of comb teeth may be provided to serve as these grooves.

A hopper 18 is disposed upwardly and in the neighborhood of one end of the driven shaft 13 of the belt conveyor 1 for feeding the capillary tubes 2 to the conveyor belt 16. FIG. 2 is a schematic section of the neighborhood of the hopper 18. Each of the tubes 2 is formed of glass, polyethylene or other plastics and is so dimensioned as to have an inner diameter of 1–1.5 mm and an overall length of 5–8 cm, the opposite ends of each of the tubes being open. Before entering the hopper 18, the insides of the capillary tubes are coated with the immunoreactive substance, such as an antibody or the like, by way of immersion or other means. The capillary tubes drop from the hopper 18 by the force of gravity and are indexed one by one to be fed to each of the grooves 17 on the top surface of the belt where they are held in place. Then, the tubes are carried on and conveyed by the conveyor belt 16.

Consequently, no specific provision or operation or the like is required for mounting the capillary tubes 2 on the belt conveyor 1 which serves as the conveying device.

A casing 19 is provided downwardly of the neighborhood of one end of the drive shaft 12 for the belt conveyor 1 for receiving the processed capillary tubes. The fully processed capillary tubes drop from the right end of the conveyor belt 16 and are successively received in the casing 19. No specific provision or operation or the like is required for demounting the tubes 2 from the belt conveyor 1.

Numeral 3 designates a feeding device for reagent and the like which is disposed along the belt conveyor 1 and which feeds a liquid specimen to be examined and an immunoassay reagent solution and the like to the interior of the tubes 2. In this instance, the reagent feeding device comprises a supplying station 20 for supplying the successively different liquid specimens to be examined, a liquid specimen washing station 30 for washing the interior of each tube 2 after a predetermined time and for discharging the reacted liquid specimen, an enzyme labelled antibody solution supplying station 40 for feeding an immunoassay reagent solution such as an enzyme labelled antibody solution into each tube 2, a reagent washing station 50 for discharging any enzyme labelled antibody solution which has not bonded upon washing the interior of each tube 2 after a predetermined time, and an enzyme substrate solution supplying station 60 for feeding an enzyme substrate solution into each tube 2. These stations are successively arranged along the conveyor belt 16.

The liquid specimen supplying station 2 comprises a feeder device 21 operable in association with the belt conveyor 1 and a plurality of liquid specimen cylinders 22 for containing blood, spittle or urine and the like, the cylinders 22 being mounted on the feeder device. The specimen liquid forms drops at the lower end of the cylinder 22, the drops being suspended therefrom. Each of the capillary tubes 2 is filled with the liquid specimen by a capillary phenomenon which occurs immediately upon contact with the end of each tube.

According to the present invention, the capillary tubes 2 are held substantially horizontal so that the force of gravity by which the liquid in the tubes 2 would tend to flow from the interior of the tubes is smaller than the force of the surface tension by which the liquid is retained in the tubes. The liquid specimen is stable in a charged condition along the full length of the tubes 2. When the liquid specimen suspended from the lower ends of the cylinders 22 is increased by a greater volume than the internal volume of the tubes, a constant volume (equivalent to the internal volume of the tubes) is always supplied to and charged in the tubes 2.

Figure 3:
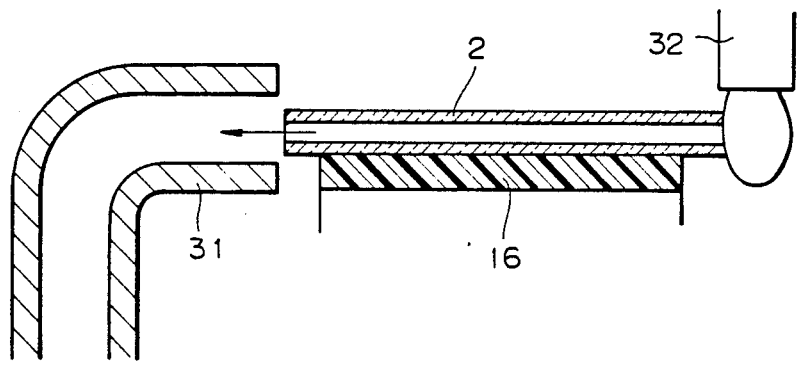
FIG. 3 is a sectional view of a station for washing a specimen to be examined.

Referring to FIG. 3 which shows the liquid specimen washing station 30 in section, this washing station will now be described in greater detail. Suction pipes 31 connected to a suction device (not shown) are disposed on one side of the conveyor belt 16 and in the proximity thereof such as not to contact the tube 2. With this non-contact arrangement, no impurities are attached to the tubes, thereby ensuring that an accurate reaction is performed. A cylinder 32 for containing washing liquid is provided on the other side of the conveyor belt 16 and forms drops at the lower end of the cylinder 32. The capillary tubes 2 are filled with washing liquid by a capillary phenomenon when the ends of the tubes contact the drops.

The suction device is controlled by, for instance, a micro-processor or the like, and is actuated in association with the movement of the belt conveyor 1. After the tubes 2 have been filled with the liquid specimen via the liquid specimen cylinder 22, the suction device is caused to suck and discharge the liquid with a lapse of a predetermined time (for instance, 10 min.), and further to continuously for intermittently suck the washing liquid from the tubes 2 for a fixed time, thereby washing the interior of the tubes 2.

The enzyme labelled antibody solution supplying station 40 is provided with a cylinder 42 similar to the washing liquid cylinder 32 on one side of the conveyor belt 16. The capillary tubes 2 as washed are filled with the enzyme labelled antibody solution by a capillary phenomenon. The enzyme labelled antibody solution is in a stable condition while the tubes 2 are filled with the antibody solution over the entire length thereof, thereby always supplying and charging a constant volume (equivalent to the internal volume of the tubes) into the tubes 2.

The reagent washing station 50 is similar to the liquid specimen washing station 30 in structure. The capillary tubes 2 are filled with the enzyme labelled antibody solution by the antibody solution cylinder 42. The solution in the tubes is sucked and discharged with a lapse of a predetermined time, thereby washing the interior of the tubes.

The enzyme substrate solution supplying station 60 is of the same structure as that of the enzyme labelled antibody solution supplying station 40 and is adapted to charge an enzyme substrate solution into the capillary tubes 2. In this instance, the tubes 2 are always filled and supplied with a constant volume (equivalent to the internal volume of the tubes) of the enzyme substrate solution.

Numeral 7 is a measuring device which is disposed such as to cover the conveyor belt 16 in the proximity of the right end thereof for measuring the optical density of the reactive solution in each tube 2. In this connection, it is noted that a spectrophotometer, a fluorophotometer or the like may be used as the measuring device. The antigen concentration in the liquid specimen is calculated by a microcomputer on the basis of the optical density of the reactive solution. Numeral 72 is an indicator for digitally displaying the result of the measurement.

Figure 4:
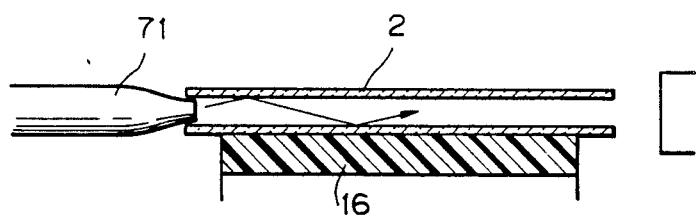
FIG. 4 is a schematic view of one form of a light emission station.

For measuring the optical density of the reactive solution as shown in FIG. 4, an optical fiber 71 having a tapered emitting end is inserted into the end of each tube 2 to emit light. The light which passes through the entire length of each tube 2 may thus be detected. In this manner, the fiber emitting end is inserted into the end of each tube 2 so that any light emitted is reflected by the inner periphery wall and passes therethrough. This will prevent any excess light which may otherwise pass through the blank for each tube from being incident, thereby ensuring an accurate measurement. As shown in FIG. 11, the light as detected may pass vertically through each tube 2 which is held horizontal on the conveyor belt 16.

Now, operation of the aforementioned embodiment will be explained by quoting an example in which an enzyme immunoassay is carried out on a carcinoembryonic antigen (hereinafter referred to as "CEA"), wherein the CEA concentration in the liquid specimen is to be measured.

Coated to the capillary tubes are an anti-CEA antibody as an immunoreactive substance, an enzyme labelled anti-CEA antibody as an enzyme labelled antibody, hydrogen peroxide as a substrate, orthophenylenediamine as a color producing reagent, and peroxidase as a labelled enzyme.

The capillary tubes 2 are adapted to allow the anti-CEA antibody to be coated to their interior surfaces and are put in the hopper 18. The liquid specimen is contained in each liquid specimen cylinder 22 and is mounted on the feeder device 21 of the liquid specimen supplying station 20.

Upon movement of the belt conveyor 1, the capillary tubes 2 are successively indexed to fall out of the hopper 18 as the conveyor belt 16 moves. The tubes 2 are held horizontal, one by one, in the respective grooves 17 formed in the belt, and are then conveyed by the conveyor belt 16.

The capillary tubes 2 at the liquid specimen supplying station 20 are filled with the liquid specimen so that the CEA contained in the specimen are bonded to the anti-CEA antibody coated to the inner surface of each tube 2, thereby performing the immunoreaction.

The conveyor belt 16 is gradually and slowly moved while the tubes 2 proceed with the immunoreaction taking place therein. With the lapse of a predetermined time (for instance, 10 min.) after the tubes have been filled with the liquid specimen, the tubes 2 at the liquid specimen washing station 30 are washed so as to discharge the liquid contained therein other than the CEA bonded to the anti-CEA antibody.

At the enzyme labelled antibody solution supplying station 40, the capillary tubes 2 are filled with the enzyme labelled anti-CEA antibody, and the enzyme labelled CEA antibody is coated to the inner surface of the tubes in a sandwich fashion by virtue of the CEA coated to the inner surface of the tubes. The tubes 2 are washed at the enzyme labelled antibody washing station 50 after the lapse of a predetermined time (for instance, 10 min.) and all the enzyme labelled antibody solution which has not been bound in the tubes is washed away.

Subsequently, at the enzyme substrate solution supplying station 60, a mixture solution of hydrogen peroxide and orthophenylenediamine is charged into each tube 2 so that oxygen which is formed from hydrogen peroxide by the enzyme (peroxidase) of the enzyme labelled antibody coated in each tube 2 reacts with the orthophenylenediamine whereby the reactive solution produces a color.

In the aforementioned reaction processes, the capillary tubes 2 are always held substantially horizontal and in a stable manner in the grooves 17 formed in the conveyor belt 1. When the capillary tubes are filled with various reagents, these reagents are retained in the tubes by a capillary phenomenon over the entire length of the tubes without voids. Accordingly, the volume of the reagents to be used for reaction is equivalent to the internal volume of the tubes, thereby ensuring an accurate reaction without requiring any measuring device.

The colored capillary tubes 2 are moved to the measuring device 7 after a predetermined time (for instance, 10 min.) has elapsed, and then the result of the reaction is read from the tubes by a chromometer. The value of what is read is computed by a microcomputer and the like and is digitally displayed by, for instance, an indicator 72.

The capillary tubes 2 which have been subjected to all the processes drop from the right end of the conveyor belt 16 and are successively received in the casing 19.

The aforementioned embodiment will now be described by exemplifying a case in which an AFP (α-fetoprotein) concentration in the liquid specimen is measured by the immunoassay of AFP.

Coated to the capillary tubes are an anti-AFP antibody as the immunoreactive substance, an enzyme labelled anti-AFP antibody as the enzyme labelled antibody, hydrogen peroxide as the enzyme substrate, orthophenylenediamine as the color producing reagent, and peroxidase as the labelled enzyme.

The anti-AFP antibody is coated to the inner surface of each tube 2 and then the inner surface of each tube is further coated with the enzyme labelled antibody. The capillary tubes are frozen, dried, and accommodated in the hopper 18. The liquid specimen is contained in each of the liquid specimen cylinders 22 and is mounted on the feeding device 21 of the liquid specimen supplying station 20.

When the belt conveyor 1 is actuated, the capillary tubes 2 drop out of the hopper 18 as the conveyor belt 16 is moved and are then held one by one substantially horizontal and in parallel with each other in the grooves 17 formed in the belt. The tubes 2 are then conveyed by the conveyor belt 16.

At the liquid specimen supplying station 20, each tube 2 is filled with the liquid specimen to allow the immunoreaction to be performed.

The conveyor belt is slowly moved while within each tube 2 the anti-AFP antibody coated to the inner surface thereof promotes a reaction with the AFT present in the liquid specimen and the immunoreaction of the AFP, which has reacted on the anti-AFP antibody coated to the inner surface of each tube, with the enzyme labelled anti-AFP antibody proceeds After a predetermined time (for instance, 15 min.) has elapsed following replenishment of the liquid specimen, each tube 2 is washed at the reagent washing station in order to discharge any liquid which is not involved in the reactions of the AFP bonded to the anti-AFP antibody bonded to the inner surface of each tube and of the enzyme labelled anti-AFP antibody bonded by the AFP.

Since the reactions are performed all at once up to this stage, the liquid specimen washing station 30 and the enzyme labelled antibody solution supplying station 40 are kept out of operation.

Subsequently, at the enzyme substrate solution supplying station 60, a mixture solution of hydrogen peroxide and orthophenylenediamine is charged into each tube 2 so that oxygen which is formed from hydrogen peroxide by the enzyme (peroxidase) of the enzyme labelled antibody coated in each tube 2 reacts on orthophenylenediamine to cause the liquid to produce a color.

The colored capillary tubes 2 are moved to the measuring device 7 after the lapse of a predetermined time (for instance, 10 min.) and then the result of the reaction is read from the tubes by a chromometer. The value of what is read is computed by a microcomputer and the like and is digitally displayed by, for instance, an indicator 72.

The capillary tubes 2 which have been subjected to all the processes drop from the right end of the conveyor belt 16 and are successively received in the casing.

Figure 5:
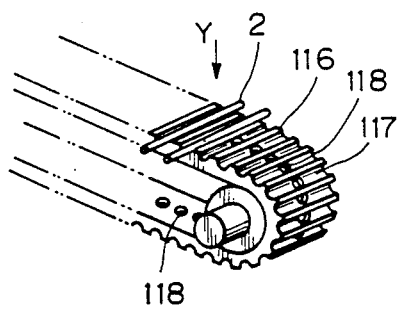
FIGS. 5 and 6 are partial perspective views showing different forms of a belt conveyor.
Figure 6:
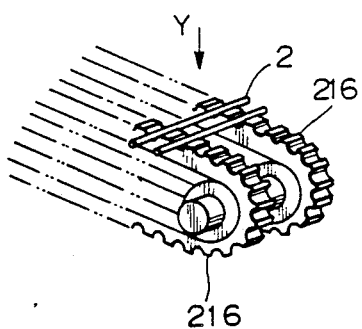

FIGS. 5 and 6 show a modified form of a belt conveyor used as the conveyor device.

For the purpose of measuring the optical density of the reaction solution by means of the measuring device 7 in order to emit a measuring beam perpendicular (Y-direction) to the instant apparatus, perforations 118 are formed on the bottoms of grooves 117 in a conveyor belt 116 to allow the beam to pass through the perforations as shown in FIG. 5. Alternatively a pair of conveyor belts 216 with the tubes 2 carried thereon are spaced away from each other in parallel therewith to allow the measuring beam to pass through clearances defined by the belts and tubes as shown in FIG. 6.

Figure 7:
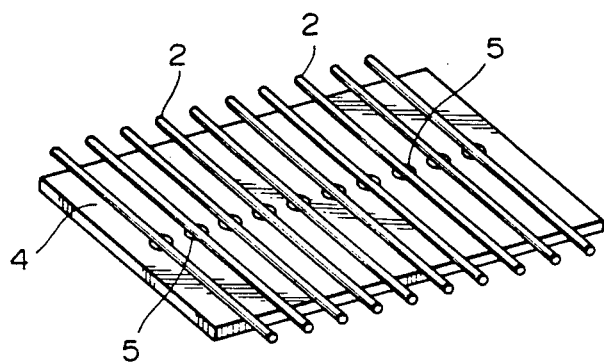
FIG. 7 is a perspective view showing a plurality of capillary tubes fixed to a sheet.

Although the embodiments have been described with reference to capillary tubes which are successively supplied one by one, as shown in FIG. 7, a plurality of the tubes 2 may be arranged in parallel with each other on a sheet 4 and the like made of paper or plastic and may be bonded, mounted or joined by an adhesive or any other suitable means. This will enable one to enter various legends, displays and records in the sheet for convenience of practical use. Numeral 5 is an aperture through which the measuring beam passes.

Figure 8:
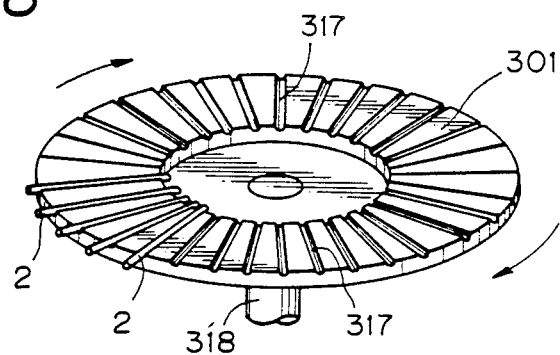
FIG. 8 is a partial perspective view showing another embodiment of a conveying device.
Figure 9:
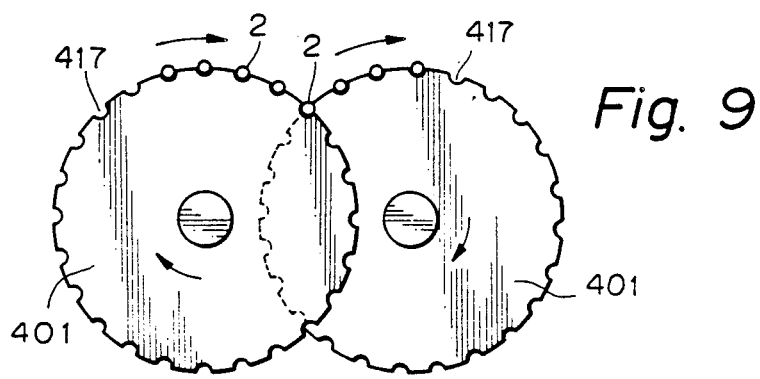
FIG. 9 is a plan view of a different embodiment of the conveying device.
Figure 10:
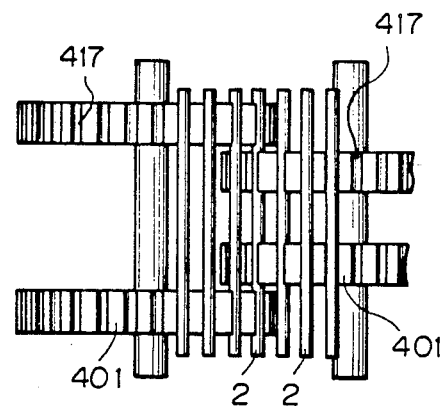
FIG. 10 is a plan view of the same.

Although the belt conveyor is used in this embodiment as a conveyor device, the invention is not limited thereto. As shown in FIG. 8, for example, a disc 301 in the doughnut form for rotating the conveyor device, may be provided on its surface with radial grooves 317 to carry the tubes 2 thereon. 318 is a rotating shaft. In this instance, it is also convenient for various controls to hold the capillary tubes by the conveyor device at regular intervals (equal angles). As is similar to the arrangement shown in FIG. 7, a plurality of the capillary tubes may be radially mounted on the sheet in advance. The chemical reaction apparatus of the present invention, as shown in FIGS. 9 and 10 may use another form of a conveyor apparatus in which a circular rotary member 401 is rotatable upon the horizontal axis and is provided on its periphery with grooves 417 to receive therein the capillary tubes 2 to be conveyed.

Although the embodiments have been described with respect to the immunoreaction apparatus embodying the present invention, the invention may include those applicable to various types of the chemical reaction apparatus.

According to the chemical reaction apparatus of the invention, the capillary tubes are horizontally held to perform the chemical reaction so that the volume of reagent and the like which are supplied to and filled in the tubes for use in reaction are always constant thereby performing a very accurate chemical reaction without requiring any metering device. Accordingly, the apparatus may be simplified to not only reduce production costs but also enable anyone to readily use it thereby facilitating maintenance of the apparatus. Advantages derived from the instant apparatus are in that either &he device for holding the tubes in the conveyor device or another device for demounting the tubes is very simple in structure and operation for convenience to its use. Thus, the chemical reaction apparatus may be obtained which is suitable for automatic chemical reaction and is ready for use.

In FIG. 12, there is shown a back side of the sheet fixedly mounted with the capillary tubes. There, to a surface side of the sheet 4 made from paper or plastic materials, there are fitted a plurality of (for example, ten, as illustrated in the drawing) capillary tubes so that they are aligned to each other with equal distances therebetween and so that their both ends extend outwardly a little from the sheet 4. The capillary tubes are same in their shapes and sizes, and are coated at their inner front surfaces with an immunoreactive substance. While the tubes 2 are fixed onto the sheet 4 in this invention most commonly by an adhesive, they may be fixed by any other conventional means such as heat welding, or they may be made integral with the sheet 4 by means of an integral plastic molding method.

On the back side of the sheet 4, there are formed columns 6 in which necessary data for each tubes can be written. The columns 6 are consisted of printed frames of a predetermined shape within which the data can be recorded by pencil, ball-point pen, and the like. Said columns 6 could of course be eliminated totally or partially or could be provided only on the front side of the sheet 4, or would be provided on the both sides. It is feasible that data are printed onto the columns automatically with the operation of a chemical reaction treating apparatus. Numeral 5 indicates windows through which light is transmitted.

Figure 13:
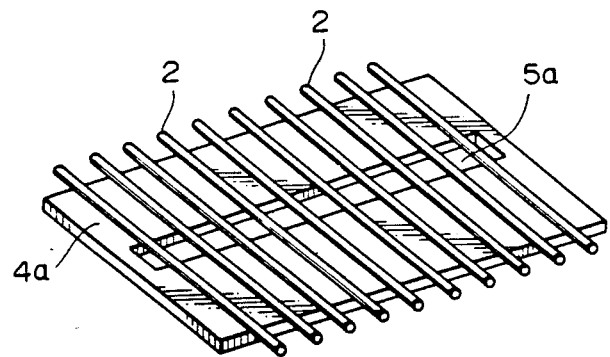
FIG. 13 is a perspective view showing another embodiment of the sheet with the capillary tubes.

Said light-transmission windows could be made continuous as shown in FIG. 13, to form a continuous slit opening 5a or any other desired shape. Or, the sheet 4a could be made by itself as light-transmissible.

Figure 14:
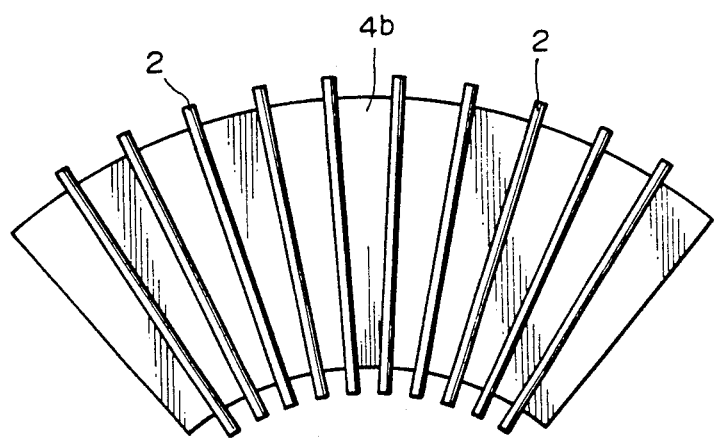
FIG. 14 is a plan view showing a still another embodiment of the sheet fixed with the tubes.

In FIG. 14, there are shown the plurality of capillary tubes 2 which are aligned to each other with an equal angular distance on a fan-like shaped sheet 4b. This kind of arrangement of capillary tubes can advantageously be employed in connection with the conveying device shown in FIG. 8.

The employment of a plurality of capillary tubes which are aligned under a predetermined pattern as a unit as described above, enables it for an operator to deal with them readily in order and in alignment by unit by unit so that the capillary tubes can always be distinguished to each other. Chemical reactions thereby can be made very accurately since the capillary tubes can hardly make a contact to each other, and can never be mixed to each other. In addition to these effects, there are several other advantageous points including that data on each capillary tubes can readily and easily be recorded on a very sheet on which the tubes are mounted.

It will be appreciated that the invention is not limited to use of the particular construction illustrated, but includes variants and alternatives within the spirit and scope of the claims.

What is claimed is:

1. A chemical reaction apparatus comprising:
   a plurality of capillary tubes,
   a conveying means for holding said capillary tubes substantially horizontally and for conveying said tubes along a conveyance path,
   feeding means mounted along said conveyance path for feeding a liquid for use in a chemical reaction to the interior of said capillary tubes, said feeding means including at least one vertically disposed liquid specimen cylinder for containing a liquid specimen so that drops of said liquid specimen are suspended from a lower end thereof, said liquid specimen cylinder being mounted so that an end of each said capillary tube is sequentially disposed immediately adjacent said lower end as said capillary tubes are conveyed along said conveyance path so that said end of said capillary tube is brought into contact with a drop of liquid specimen suspended from said liquid cylinder whereby each capillary tube is filled with liquid specimen by capillary phenomena immediately upon contact of the drop with said end of each said tube;
   washing means mounted along said conveyance path for washing said liquid from the interior of said tubes;
   enzyme labeled antibody solution supplying means mounted along said conveyance path for feeding an enzyme labeled antibody solution to the interior of said capillary tubes; and
   enzyme substrate solution supplying means mounted along said conveyance path for supplying an enzyme substrate solution to the interior of each of said capillary tubes.

2. A chemical reaction apparatus as recited in claim 1 wherein a plurality of said capillary tubes are held in parallel with each other by said conveying means.

3. A chemical reaction apparatus as recited in claim 1 wherein inner surfaces of said capillary tubes are previously coated with an immunoreactive substance, said feeding means for feeding a liquid being adapted to feed said liquid to the interior of each of said capillary tubes at a predetermined interval.

4. A chemical reaction apparatus as recited in claim 1 wherein a plurality of said capillary tubes are radially held by said conveying means.

5. A chemical reaction apparatus as recited in claim 4 wherein a plurality of said capillary tubes are held at a fixed distance by said conveying means.

6. A chemical reaction apparatus as recited in claim 5 wherein said capillary tubes are previously coupled to the conveying means.

7. A chemical reaction apparatus as recited in claim 6 wherein said conveying means is a belt conveyor, and wherein a belt for said belt conveyor is provided with grooves to hold therein said capillary tubes.

8. A chemical reaction apparatus as recited in claim 5 wherein said conveying means is a circular rotary member with grooves on the periphery thereof, said capillary tubes being held in said grooves and conveyed thereby.

9. A chemical reaction apparatus as recited in claim 8 wherein said feeding means brings at least one of a liquid specimen or a liquid reagent and said washing means brings a washing liquid, respectively, into contact with the ends of said capillary tubes, and wherein said capillary tubes are filled with said liquid specimen or reagent and said washing liquid by a capillary phenomenon.

10. A chemical reaction apparatus as recited in claim 1 wherein said washing means includes a sucking means to suck and discharge said liquid reagent specimen or without contact with said capillary tubes.

11. A chemical reaction apparatus as recited in claim 10 wherein said sucking means for said washing means includes a washing liquid supplying means on the side reverse to said capillary tubes.

12. A chemical reaction apparatus as recited in claim 1, in which the plurality of said capillary tubes are fixedly mounted under a predetermined alignment on a sheet on which there are formed portions for recording data for the tubes.

13. A chemical reaction apparatus as recited in claim 12, in which the capillary tubes are aligned on the sheet with an equal distance therebetween.

14. A chemical reaction apparatus as recited in claim 12, in which the capillary tubes are aligned on the sheet with an equal angular distance therebetween.

15. A chemical reaction apparatus as recited in claim 12, in which the capillary tubes are fixed upon one of the surfaces of sheet.

16. A chemical reaction apparatus as recited in claim 12, in which both ends of the tubes fixed on the sheet extend laterally outwardly from the sheet.

17. A chemical reaction apparatus as recited in claim 12, in which an immunoreactive substance is coated in an inner front surface of the capillary tubes.

18. A chemical reaction apparatus as recited in claim 12, in which light-transmission windows are provided to the sheet at its portions over which the capillary tubes overlap.

19. A chemical reaction apparatus as recited in claim 12, in which a light-transmission slit is provided to the sheet, extending continuously and throughout its portions over which the capillary tubes overlap.

20. A chemical reaction apparatus comprising:
    a plurality of capillary tubes;

a conveying means for holding said capillary tubes substantially horizontally and for conveying said tubes along a conveyance path, feeding means mounted along said conveyance path for feeding a liquid for use in a chemical reaction to the interior of said capillary tubes, said feeding means including at least one vertically disposed liquid specimen cylinder for containing a liquid specimen so that drops of said liquid specimen are suspended from a lower end thereof, said liquid specimen cylinder being mounted so that an end of each said capillary tube is sequentially disposed immediately adjacent said lower end as said capillary tubes are conveyed along said conveyance path so that said end of said capillary tube is brought into contact with a drop of liquid specimen suspended from said liquid cylinder, whereby each capillary tube is filled with liquid specimen by capillary phenomena immediately upon contact of the drop with said end of each said tube;

washing means mounted along said conveyance path for washing said liquid from the interior of said tubes;

enzyme labeled antibody solution supplying means mounted along said conveyance path for feeding an enzyme labeled antibody solution to the interior of said capillary tubes; and enzyme substrate solution supplying means mounted along said conveyance path for supplying an enzyme substrate solution to the interior of each of said capillary tubes, and a measuring means for measuring the result of a chemical reaction in said capillary tubes.

21. A chemical reaction apparatus as recited in claim 20 wherein inner surfaces of said capillary tubes are previously coated with an immunoreactive substance, said feeding means for feeding a liquid being adapted to feed said liquid to the interior of each of said capillary tubes at a predetermined interval.

22. A chemical reaction apparatus as recited in claim 20 wherein said measuring means includes an optical density measuring means to measure an optical density of a reaction solution in each of said capillary tubes.

23. A chemical reaction apparatus as recited in claim 22 wherein said optical density measuring means an optical fiber the emitting end of which is tapered and inserted into the end of each of said capillary tubes, said optical density measuring means being adapted to detect a light emitted from said optical fiber and passing through said capillary tubes along the entire length thereof.

24. A chemical reaction apparatus as recited in claim 22 wherein said optical density measuring means is adapted to detect a transmitted light caused when a measuring beam traverses perpendicular to said capillary tubes.

25. A chemical reaction apparatus comprising:

a plurality of capillary tubes, conveying means for holding said capillary tubes substantially horizontally and for conveying said tubes along a conveyance path; and feeding means mounted along said conveyance path for feeding a liquid for use in a chemical reaction to the interior of said capillary tubes, said feeding means including at least one vertically disposed liquid specimen cylinder for containing a liquid specimen so that drops of said liquid specimen are suspended from a lower end thereof, said liquid specimen cylinder being mounted so that an end of each said capillary tube is sequentially disposed immediately adjacent said lower end as said capillary tubes are conveyed along said conveyance path so that said end of said capillary tube is brought into contact with a drop of liquid specimen suspended from said liquid cylinder, whereby each capillary tube is filled with liquid specimen by capillary phenomena immediately upon contact of the drop with said end of each said tube.

* * * * *